(12) United States Patent
Bowden

(10) Patent No.: US 7,207,329 B2
(45) Date of Patent: Apr. 24, 2007

(54) SYRINGE AND MULTI-DOSE INHALER ADAPTER FOR A VENTILATOR

(75) Inventor: Kevin D. J. Bowden, Orangeville (CA)

(73) Assignee: O-Two Systems International Inc., Mississauga, Ontario (CA)

( * ) Notice: Subject to any disclaimer, the term of this patent is extended or adjusted under 35 U.S.C. 154(b) by 525 days.

(21) Appl. No.: 10/691,587

(22) Filed: Oct. 24, 2003

(65) Prior Publication Data

US 2004/0089296 A1   May 13, 2004

(51) Int. Cl.
  *A61M 15/00* (2006.01)
  *A61M 16/00* (2006.01)
(52) U.S. Cl. .............................. 128/203.12; 128/203.28
(58) Field of Classification Search ........... 128/200.14, 128/200.21, 200.22, 200.23, 202.27, 203.12, 128/203.13, 203.15, 204.25, 207.15, 207.16, 128/912
  See application file for complete search history.

(56) References Cited

U.S. PATENT DOCUMENTS

| | | | |
|---|---|---|---|
| 4,953,547 A * | 9/1990 | Poole, Jr. ............... | 128/203.12 |
| 5,297,543 A * | 3/1994 | Larson et al. .......... | 128/200.23 |
| 5,762,063 A | 6/1998 | Coates et al. | |
| 5,791,340 A | 8/1998 | Schleufe et al. | |
| 5,996,579 A | 12/1999 | Coates et al. | |
| 7,059,322 B2 * | 6/2006 | Rich et al. ............. | 128/200.24 |
| 2004/0055596 A1 * | 3/2004 | Bacon ................... | 128/200.23 |
| 2005/0279362 A1 * | 12/2005 | Colman et al. ........ | 128/207.14 |

* cited by examiner

*Primary Examiner*—Teena Mitchell
*Assistant Examiner*—Amadeus Lopez
(74) *Attorney, Agent, or Firm*—Paul J. Field

(57) ABSTRACT

An adapter for disposition in a breathing system circuit between a source of breathable gas and a patient airway circuit, the adapter having: a tube with a side wall defining a breathing passage between a tube inlet and a tube outlet; an injector conduit extending laterally through the tube side wall having: a bore; a nozzle communicating between the bore and the passage; and an external port, where the port includes: syringe connector means for releasably sealing between the bore of the injector conduit and a syringe; and multiple dose inhaler connector means for releasably connecting the bore of the injector conduit and a multiple dose inhaler.

8 Claims, 5 Drawing Sheets

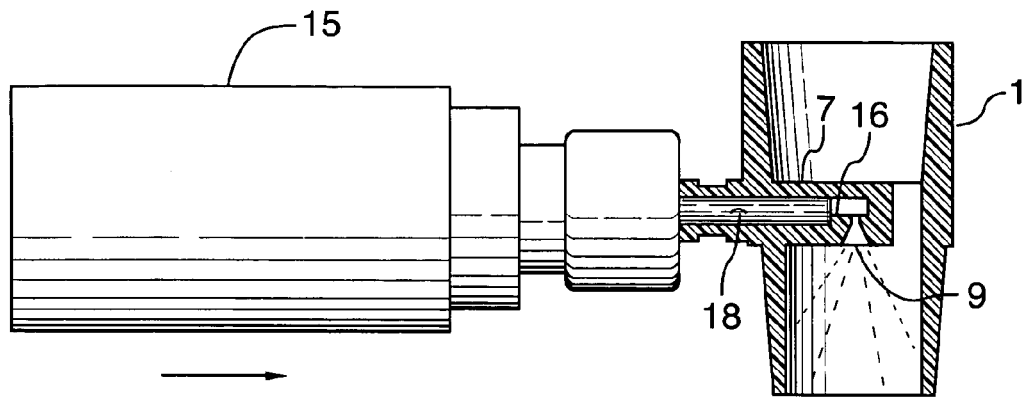
FIG.3
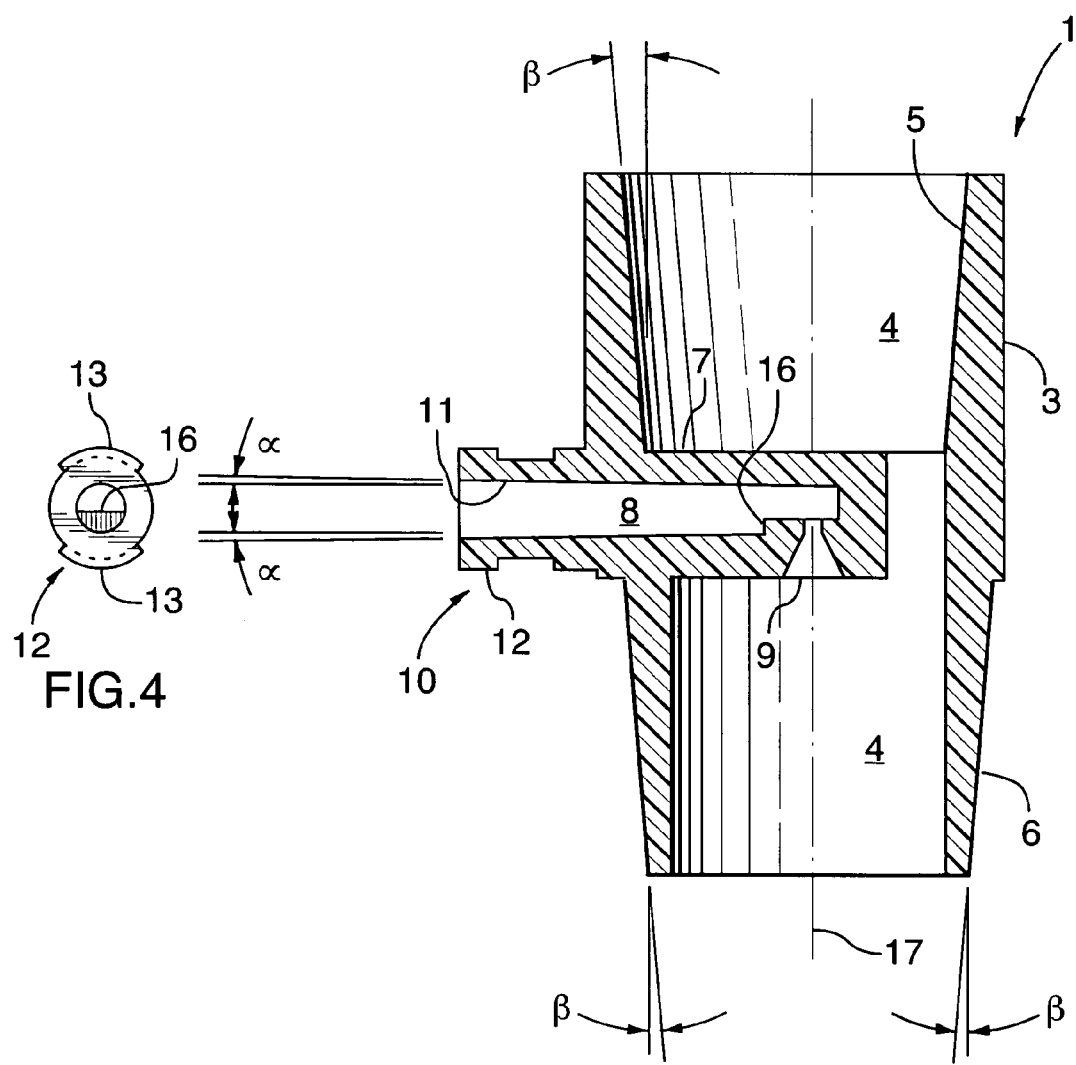
FIG.4
FIG.5

SYRINGE AND MULTI-DOSE INHALER ADAPTER FOR A VENTILATOR

TECHNICAL FIELD

The invention relates to a breathing system medicament injection adapter with a dual purpose port having a Luer taper and Luer lock for connecting a syringe and a central bore adapted for receiving a multi-dose inhaler nozzle.

BACKGROUND OF THE ART

During the treatment of patients in cardiac/respiratory arrest or respiratory distress, medication may be introduced into the lungs for absorption into the blood stream. The medication can take the form of a liquid that is injected into the patients airway via the breathing tube placed into the patient's trachea or via a Multi Dose Inhaler where a dispersed spray of the drug to be absorbed is "puffed" into the breathing tube.

Devices have been provided individually for either of these two means of delivery however no single device has allowed the healthcare worker to select either method or indeed to introduce different drugs by either methods into the airway of the same patient.

For example, U.S. Pat. Nos. 5,996,579 and 5,762,063 to Coates et al provide two separate ports for administering medicament via syringe through a narrow port and via a nebulizer through a wide mouth port. Use of two separate ports requires individual sealing with caps, complicates the manufacture and use of the device and does not ensure adequate mixing of the medicament with the flow of gas for proper delivery to the patient.

U.S. Pat. No. 5,791,340 to Schleufe et al provides a port for mixing medicament from a multiple dose inhaler into the interior of the bag of a bag-valve-mask ventilator. However delivery to the patient is impeded since the bag contents must pass through a valve to the patient airway and a large portion of the medicament remains as a coating within the bag and on the valve surfaces.

It is an object of the invention to provide a medicament administration adapter designed to fit within any breathing circuit or to be able to be attached to any resuscitation/ventilation device.

It is a further object that such an adapter provide a single port connection for the insertion of medicament via both a syringe and a multi-dose inhaler canister (MDI).

Further objects of the invention will be apparent from review of the disclosure, drawings and description of the invention below.

DISCLOSURE OF THE INVENTION

The invention provides a breathing system medicament injection adapter with a dual purpose port with Luer taper/Luer lock for connecting a syringe and a central bore adapted for receiving and manually actuating a multi-dose inhaler. The adapter is placed in a breathing system circuit between a manually operated bag-valve-mask or an automatic ventilator (as a source of breathable gas) and the patient airway circuit. The adapter includes a tube with a breathing passage and a dual purpose injector conduit extending laterally through the tube side wall with a bore, a nozzle coaxial with the passage and an external dual purpose connection port. The port includes a syringe connector (such as, a female Luer tapered bore surface and a male Luer lock) and multiple dose inhaler connector including an actuation abutment extending into the bore to release a dose when the inhaler is manually squeezed. The medicament is released downstream through the nozzle into the center of the breathable gas flow, mixed in the turbulent gas flow rather than adhering to passage walls and is delivered to the patient more effectively.

DESCRIPTION OF THE DRAWINGS

In order that the invention may be readily understood, two embodiments of the invention are illustrated by way of example in the accompanying drawings.

FIGS. 1–5 show a first embodiment where FIG. 1 is an axial cross sectional view through a typical bag valve mask assembly showing the flow of air through a rear valve into the bag and out through a conical exit port toward the adapter which is positioned between the outlet port and the patient airway such as an esophageal tube or face mask.

FIG. 2 is a detailed sectional view showing the adapter with a syringe mounted to the Luer connectors on the lateral port.

FIG. 3 is a like view showing a multiple dose inhaler mounted to the interior of the port.

FIG. 4 is a detailed view of the Luer lock connector.

FIG. 5 is a detailed sectional view of the adapter.

FIG. 6 is a sectional view showing the MDI and MDI adapter installed in the port.

FIGS. 7 and 8 are perspective views thereof.

FIG. 9 is a perspective view showing the MDI adapter withdrawn for use with a syringe.

Figure 1:
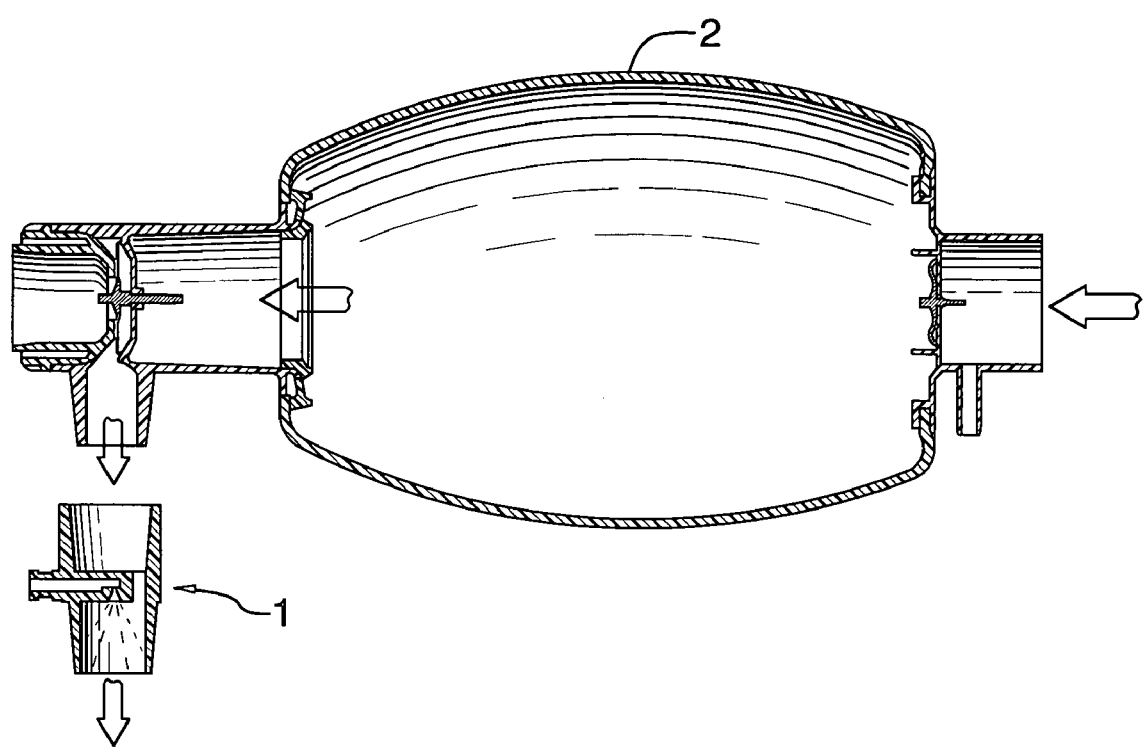

Further details of the invention and its advantages will be apparent from the detailed description included below.

DETAILED DESCRIPTION OF PREFERRED EMBODIMENTS

As shown in the Figures, the disposable single use adapter 1 allows the delivery of medication by syringe 14 injection or Multi Dose Inhaler 15 into the patient breathing system by its insertion into a resuscitation, ventilation or anesthetic breathing circuit such as a Bag Valve Mask Resuscitator 2 or automatic patient ventilator. The adapter 1 consists of a short tube 3 with a 22 mm Internal Diameter conical connector at one end 5 and a 22 mm External Diameter X 15 mm internal diameter conical connector at the other end 6. Both conical connectors 5, 6 are designed to conform to the requirements of ISO 5356-1 Conical Connectors. At the mid point of the tube 3 a lateral injector conduit 7 is preferably positioned at 90° to the longitudinal axis 17 of the tube 3 so that the nozzle 9 at the inner end lies in the center of the tube passage 4 with an outer port 10 of the injection conduit 7 extending outside the wall of the tube 3. The outer port 10 of the injection conduit 7 has a female internal 6° Luer tapered bore 8 in accordance with the requirements of ISO 594/1. In addition the external port 10 has a male Luer Lock fitting 12 in accordance with the requirements of ISO 594-2. The central bore 8 of the injection conduit 7 terminates with an outlet nozzle 9 coaxial to the longitudinal axis 17 of the tube 3.

In the first embodiment illustrated in FIGS. 2–5, the internal bore 8 of the injection conduit 7 is stepped with an abutment 16 to engage the outlet nozzle 18 of a multi dose inhaler canister 15 when manually depressed. In the second embodiment illustrated in FIGS. 6–9, the internal bore 8 is extended using a removable MDI adapter 19, where the MDI adapter includes an abutment 20 to engage the outlet nozzle 18.

As shown in FIG. 1, the adapter 1 is disposed in a breather system circuit between the bag valve mask 2 as a source of breathable gas and the patient airway circuit (not illustrated) which is downstream of the adapter 1. To equal advantage the adapter 1 can be positioned between the patient airway circuit and an automatic ventilator. Standard conical inlet and outlet connectors 5, 6 are provided for this purpose.

Figure 2:
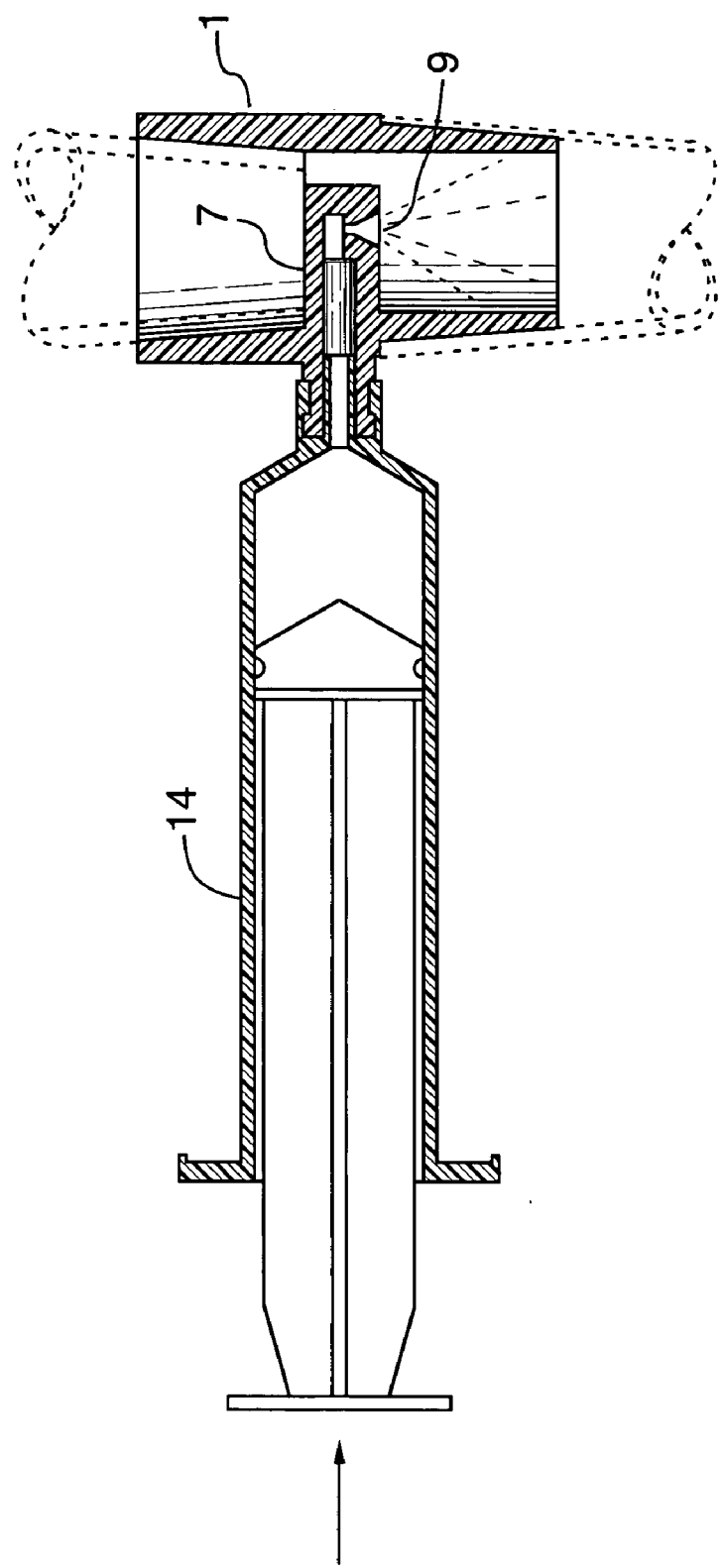

With reference to FIGS. 2 and 5, the adapter 1 comprises a tube 3 having an elongate axis 17 with side wall defining an internal breathing passage 4. The tube inlet 5 as illustrated is a female conical connection and the tube outlet 6 is a male conical connection (with walls oriented at angle β) which are standard for ventilator conduits. Conical connections 5, 6 provide a quick release and connection with sufficient sealing and interference fit to prevent accidental disconnection.

The tube 3 of the first embodiment has a dual purpose injector conduit 7 extending laterally through the tube side wall having a central bore 8 and external connection port 10. A nozzle 9 communicates between the bore 8 and the center of the passage 4 of the tube 3.

The dual purpose port 8 includes a female Luer tapered bore surface 11 (at angle α) and for positive locking includes a male Luer lock 12 on an outer end of the injector conduit 7 with two laterally extending flanges 13. As will be recognized as those skilled in the art, the male Luer lock flanges 13 engage with mating threaded surfaces on the female Luer lock surface of the syringe 14 providing a positive locking in addition to the frictional fit of the male tapered surface on the syringe with the female tapered bore surface 11.

As indicated in FIG. 3, the dual purpose injector conduit 7 has a bore 8 that permits insertion of the multiple dose inhaler nozzle 18 a distance sufficient to positively engage the abutment 16. As best shown in FIGS. 4 and 5, the abutment 16 extends partially into the bore 8 providing a stop or shoulder against which the multiple dose inhaler nozzle 18 can engage. As will be recognized by those skilled in the art, the inhaler 15 is actuated by manually squeezing against the adapter 1 to release a spray of medicament as shown in FIG. 3 through the multiple dose inhaler nozzle 18 and then through the adapter nozzle 9. A close fit between the side surfaces of MDI nozzle 18 and the tapered bore 8 seals the nozzle 18 and prevents escape of the medicament except through the nozzle 9.

The nozzle 9 shown in the drawings is a simple conical countersunk aperture disposed coaxially with the passage 4 along axis 17. As such the nozzle 9 can be easily formed with simple plastic injection techniques. A particular advantage of the invention is the thorough mixing of medicament sprayed through the nozzle 9 with the flow of gas through the passage 4. Prior art methods often result in waste of medicament which is retained on the internal walls of the periphery bag or conduit. In contrast, the invention provides improved mixing with the breathable gas as the nozzle 9 sprays the medicament centrally within the flow of gas passing through the passage 4.

Further, the use of tapered surfaces 11, abutment 16 and Luer lock 12 enables use of a single port 10 for delivery of medicament via two separate methods. A single sealing cap is required which is readily available due to the Luer lock 12 and standardization in the industry.

Figure 6:
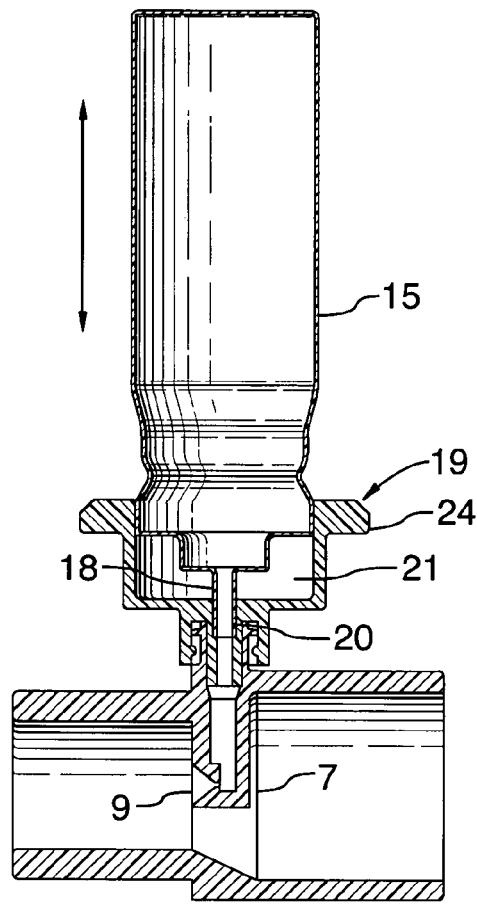
FIGS. 6–9 show a second embodiment where
Figure 7:
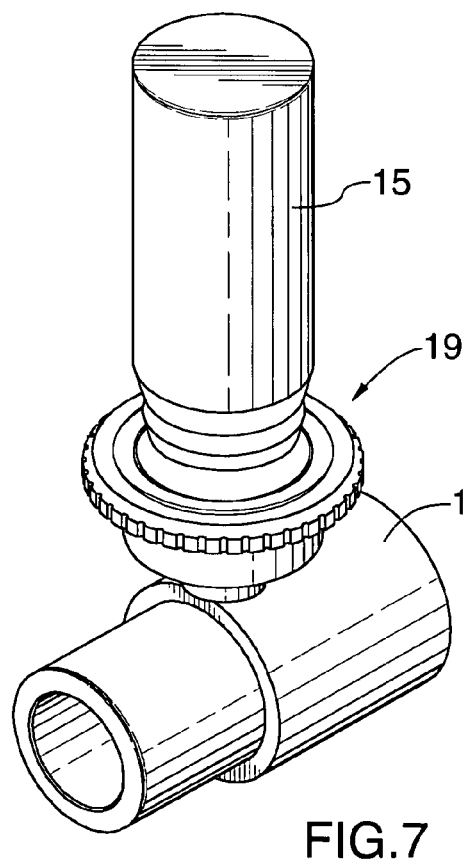
Figure 8:
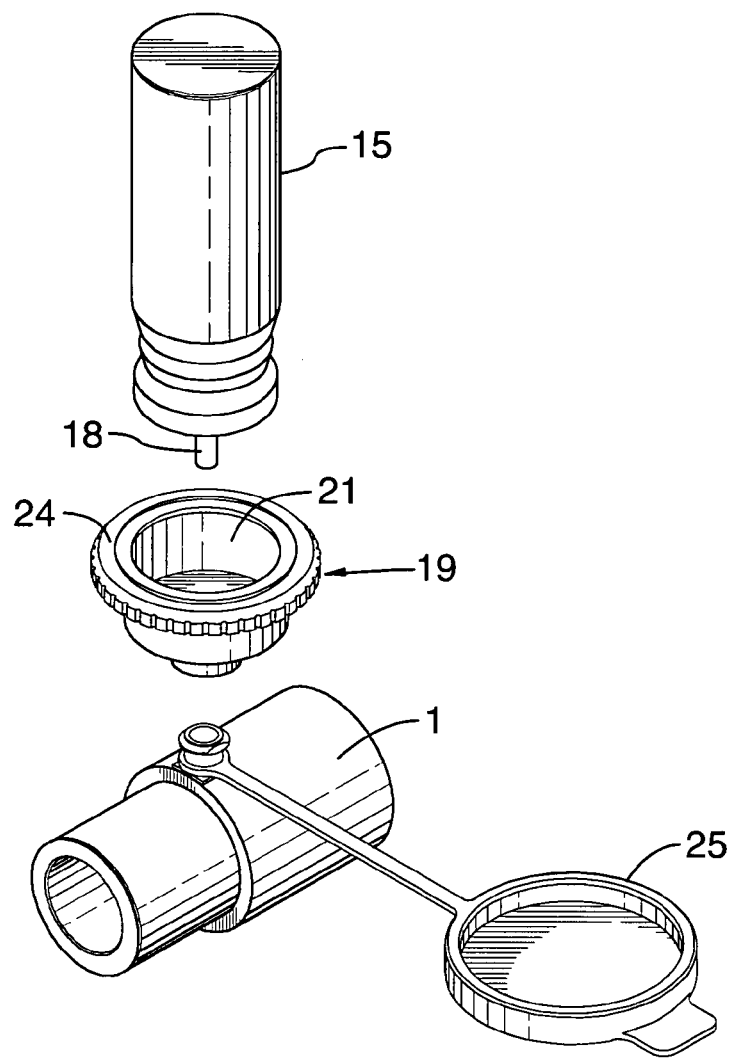
Figure 9:
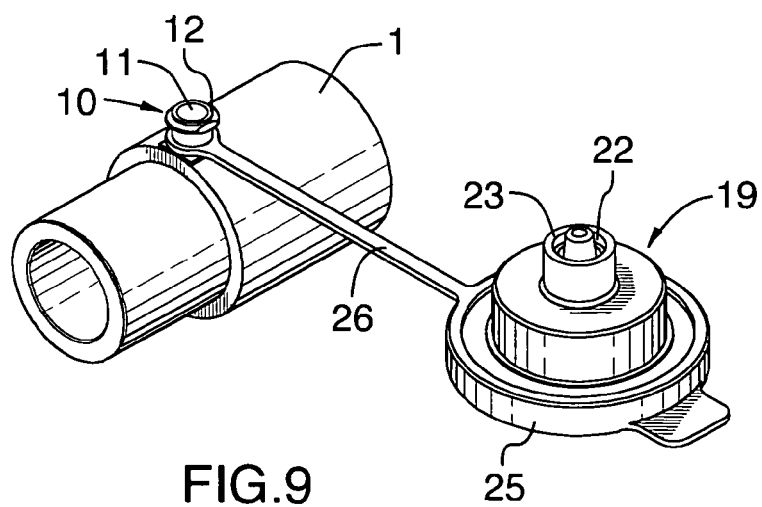

FIGS. 6–9 illustrate a second embodiment where the connection of the MDI is made with a removable MDI adapter 19. As shown in FIGS. 8–9, the MDI adapter 19 may conveniently be secured to the tube 3 with a removable cap 25 on a flexible lead 26. FIG. 6 shows the MDI 15 mounted for longitudinal sliding within a recess 21 of the MDI adapter with the MDI nozzle 18 engaging an abutment 20 for ejecting the medicament through the injector conduit 7 and nozzle 9.

The MDI adapter includes a male tapered surface 22 to engaged the female Luer tapered surface 11 of the port 10 and includes a female Luer threaded socket 23 to engage the flanges 13 of the male Luer lock 12 of the port 10. The MDI adapter preferably includes a manual grip flange 24 to accommodate the application of manual squeezing force to the end of the MDI. FIG. 7 shows the MDI adapter and MDI assembled to the tube 3, whereas FIG. 9 shows the MDI adapter 19 in a withdrawn position for attachment of a syringe 14 with Luer connector in a manner similar to that shown in FIG. 2.

Although the above description relates to a specific preferred embodiment as presently contemplated by the inventor, it will be understood that the invention in its broad aspect includes mechanical and functional equivalents of the elements described herein.

I claim:

1. An adapter for disposition in a breathing system circuit between a source of breathable gas and a patient airway circuit, the adapter comprising:
   a tube with a side wall defining a breathing passage between a tube inlet and a tube outlet;
   an injector conduit extending laterally through the tube side wall having: a bore; a nozzle communicating between the bore and the passage; and an external port;
   wherein the port includes:
   a syringe connector adapted to releasably seal between the bore of the injector conduit and a syringe, wherein the syringe connector is selected from the group consisting of: a female Luer tapered bore surface; and a male Luer lock on an outer end of the injector conduit including two laterally extending flanges; and
   a multiple dose inhaler connector adapted to releasably connect the bore of the injector conduit and a multiple dose inhaler.

2. An adapter for disposition in a breathing system circuit between a source of breathable gas and a patient airway circuit, the adapter comprising:
   a tube with a side wall defining a breathing passage between a tube inlet and a tube outlet;
   an injector conduit extending laterally through the tube side wall having: a bore; a nozzle communicating between the bore and the passage; and an external port;
   wherein the port includes:
   a syringe connector adapted to releasably seal between the bore of the injector conduit and a syringe; and
   a multiple dose inhaler connector adapted to releasably connect the bore of the injector conduit and a multiple dose inhaler, wherein the multiple dose inhaler connector comprises a removable MDI adapter releasably engagable with the syringe connector, the MDI adapter having an adapter bore in communication with the injector conduit bore and having an actuation abutment extending therein.

3. An adapter according to claim 2 wherein the multiple dose inhaler connector comprise an actuation abutment extending into the bore.

4. An adapter according to claim 2 wherein the MDI adapter includes a recess adapted for longitudinal sliding engagement of the MDI.

5. An adapter according to claim 2 wherein the syringe connector comprise a female Luer tapered bore surface and the MDI adapter includes a male tapered surface.

6. An adapter according to claim 2 wherein the syringe connector comprise a male Luer lock on an outer end of the injector conduit including two laterally extending flanges, and the MDI adapter includes a female Luer threaded socket adapted for engagement with said flanges.

7. An adapter according to claim 6 wherein the MDI adapter includes a manual grip flange.

8. An adapter according to claim 2 wherein the MDI adapter includes a cap secured to the tube.

* * * * *